United States Patent [19]

Buchas

[11] Patent Number: 4,561,448
[45] Date of Patent: Dec. 31, 1985

[54] APPARATUS FOR SENSING AND RECORDING BIOPOTENTIAL ELECTRICAL SIGNALS

[75] Inventor: Gerald L. Buchas, Bristol, Conn.

[73] Assignee: Colen-Kery, Inc., Burlington, Conn.

[21] Appl. No.: 576,488

[22] Filed: Feb. 2, 1984

[51] Int. Cl.⁴ ............................................. A61B 5/04
[52] U.S. Cl. .................................... 128/733; 128/745; 128/734
[58] Field of Search ........ 128/745, 733, 639, 731–732, 128/734

[56] References Cited

U.S. PATENT DOCUMENTS

| | | | |
|---|---|---|---|
| 3,217,706 | 11/1965 | Sullivan | 128/745 X |
| 3,946,723 | 3/1976 | Servos | 128/745 X |
| 4,155,352 | 5/1979 | Toglia | 128/733 |
| 4,320,768 | 3/1982 | Ledley et al. | 128/733 |
| 4,474,186 | 10/1984 | Ledley et al. | 128/733 |

FOREIGN PATENT DOCUMENTS 0586895 1/1978 U.S.S.R. .............................. 128/745

Primary Examiner—Lee S. Cohen
Assistant Examiner—Angela D. Sykes
Attorney, Agent, or Firm—McCormick, Paulding & Huber

[57] ABSTRACT

Electrodes located at predetermined locations about a patient's eye sense electrical signals indicative of eye movement. The sensed signals are coupled to amplification circuitry operated from a battery power supply. The battery power supply and battery operated amplification circuitry have a floating common reference to reject electromagnetic interference. An optocoupler isolates the battery operated circuitry and the patient from non-battery operated circuitry which provides a signal representative of the sensed signal to drive a recording pen of a chart recorder. Corrective compensation responsive to variations in the sensed signal caused by electrode to skin surface contact changes and circuit changes maintains a zero central fixation reference potential.

14 Claims, 4 Drawing Figures

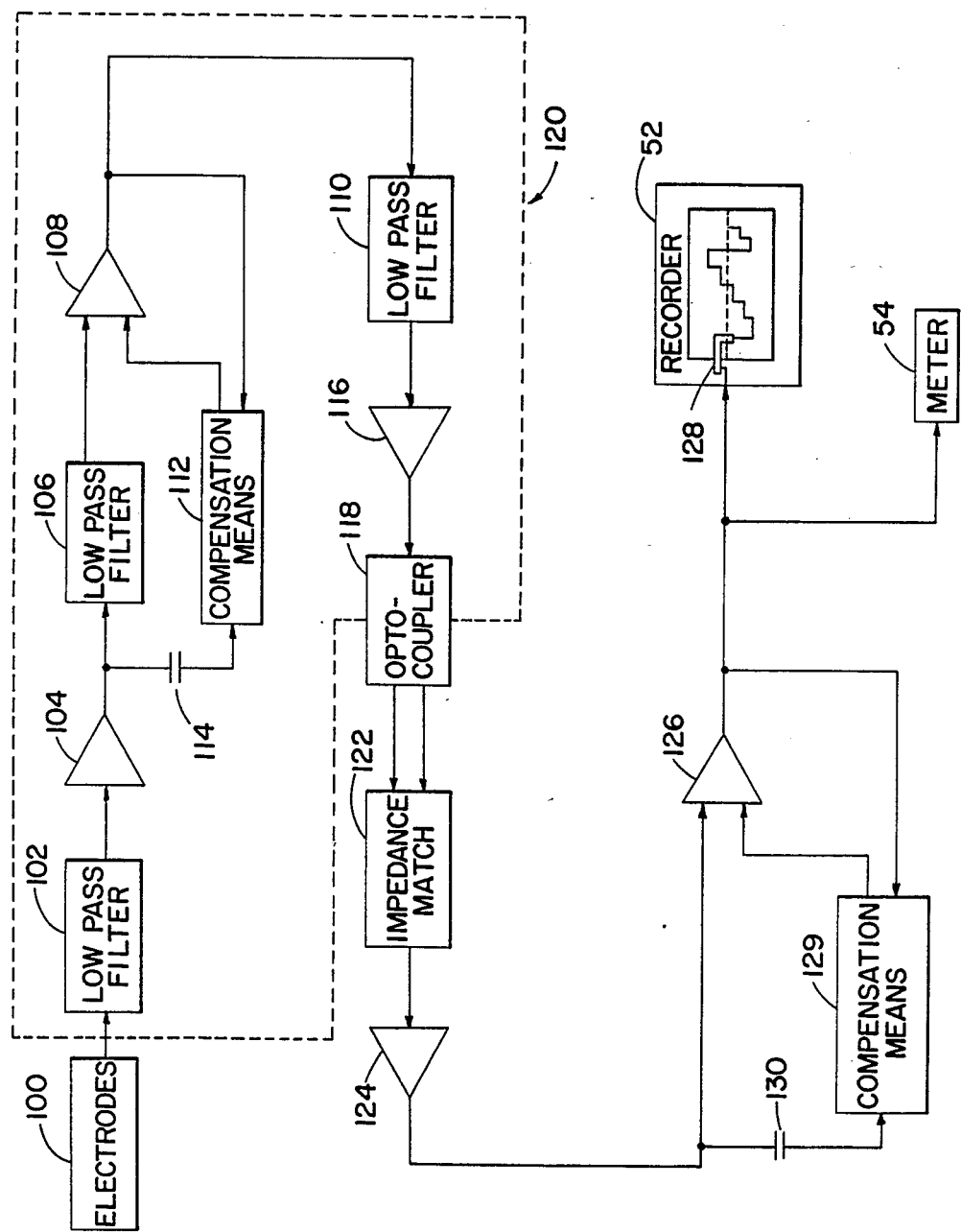
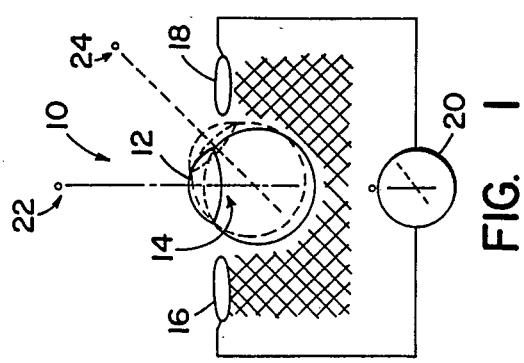
FIG. 3
FIG. 1

APPARATUS FOR SENSING AND RECORDING BIOPOTENTIAL ELECTRICAL SIGNALS

BACKGROUND OF THE INVENTION

This invention relates to measuring biopotential electrical signals particularly relating to electro-oculography and deals more specifically with apparatus for sensing and recording the ocular standing DC potentials indicative of eye movement across the eye socket.

Electro-oculography relates generally to a method of recording voltage changes due to eye movement, from pairs of electrodes attached to the body surface near the eyes and deals more specifically with the production and study of an electro-oculogram (EOG). The EOG is defined in the present disclosure to be a graphic display or record of the measurement of such voltage changes.

It is thought that the voltage developed across the eye is due to electrical activity from a retinal structure and, in particular, activity in the pigment epithelium. The pigment epithelium is the tissue that lines the back of the retina and plays a very supportive role for the retina and particularly the outer segments of the receptors. The pigment epithelium itself plays no direct role in the transmission of information from the eye to the brain. It has, however, been established that a relationship exists between the pigment epithelium and the receptors, such that, if the pigment epithelium is not functioning properly the receptors are also generally not functioning properly. Vision does not occur if the receptors are not working because only the receptors can receive and transform light into the neural activity which is sent to the brain.

The measurement of the ocular standing DC potential or change in voltage across the eye as the eye moves is based on the proposition that the eyeball is charged and behaves as an electrical dipole. Motion of the eyeball produces a varying voltage on the skin surrounding the eye and the magnitude of the voltage difference produced across the eye has been found to be nearly proportional to the position of the eye. Consequently, the EOG provides an indirect measure of the ocular standing DC potential and may be used to derive a precise, continuous record of eye position and, if desired, its time derivative, eye motion.

Measurements made heretofore have shown that the ocular standing DC potential generally ranges in magnitude from 50 to 3500 microvolts for eye fixation changes between 2.5 degrees to 90 degrees, and which average 35 microvolts per degree of eye rotation. Heretofore used DC voltage sensing and amplification means have not proven to be completely satisfactory for the sensing and recording of such low level DC voltage signals. The ocular standing DC potential is often masked in noise levels approaching several millivolts. Prior high gain DC amplifier-recorder systems generally encounter difficulties in sensing the ocular standing DC potential and its variations in noise levels exceeding 1 microvolt.

Another problem associated with the sensing and recording of the ocular standing DC potential is variations in the sensed DC voltages caused by changes in the electrode to skin surface contact. Such contact changes occur during the course of apparatus set up and patient testing and may be caused by sweating, uncleansed skin surface at the contact point and, improper electrode attachment among others. It is desirable that the influence of such skin surface contact changes be eliminated or compensated for so that any variations in the magnitude of the sensed ocular standing DC potential are attributable to voltage changes produced by eye movement.

Sullivan in U.S. Pat. No. 3,217,706 attempts to overcome some of the problems associated with low level DC voltage signal detection and changes in electrode to skin surface contact by amplitude modulating a carrier with impedance changes which occur between pairs of periorbital electrodes as the eye moves, and then demodulating the carrier to provide the representative EOG electrical potential signal and its variations.

Another drawback associated with some prior systems is that the patient under test and the sensing and recording apparatus have to be kept at the same electrical reference potential for proper apparatus operation. Generally, the patient and apparatus are electrically grounded. The patient is connected to electrical ground via an electrode attached to the skin. Systems of this type are generally very susceptible to electromagnetic interference and electrical noise pick up. These systems may also pose a safety hazard because the patient is at a ground potential and consequently, may experience an electrical shock when touching the surrounding which may be at a different electrical potential.

Another drawback to other previously used systems is the requirement of additional equipment, such as, for example, an oscilloscope, which is used to calibrate and balance the sensing and recording apparatus so that the EOG readings have equal excursions above and below a mid-graph reference line for both the left and right eyes when the left and right eyes move an equal amount.

Yet another drawback found in some other previously used systems is the necessity to continuously rebalance the recording apparatus and reposition the mid-graph reference line during testing of the patient. Repositioning of the reference line is necessary to prevent the recording media, such as, for example, a strip chart recorder pen from drifting off the chart paper during testing.

Still another drawback to other systems is the considerable expense associated with the acquisition of such sensing and recording apparatus. Hence, the simple economics of apparatus cost versus expected frequency of use tend to dictate which practitioners and/or hospitals acquire such apparatus. More often than not, practitioners who sometimes find electro-diagnostic analysis to be clinically useful, cannot justify the expense of acquiring such apparatus simply because of the relative infrequency of such occasions.

Toglia in U.S. Pat. No. 4,155,352 describes an interface unit for use with an electroencephalograph (EEG) machine as one way to make such apparatus less costly by using the recording portion of the EEG machine. Conventionally located electrodes sense the voltage signals produced about the eye. The signals are processed and then directly coupled to an EEG machine recorder inputs to produce the EOG.

Toglia also attempts to overcome the problem of noise contaminated signals by employing frequency modulation techniques to transmit and amplify the sensed signals.

Consequently, there exists a need for apparatus to sense and record biopotential electrical signals that is inexpensive, easy to use, and overcomes the limitations generally associated with other systems.

A general aim of the present invention is to provide an improved apparatus for sensing and recording the biopotential electrical signals indicative of eye movement across the eye socket.

A feature of the present invention is to provide apparatus to sense and record the ocular standing DC potential directly without the signal conversion normally associated with modulation techniques.

Another feature of the present invention is to provide apparatus which automatically compensates for variations in the sensed biopotential electrical signals caused by changes in the electrode to skin surface contact.

Other features and advantages of the present invention will be apparent from the following written description and the drawings forming a part hereof.

SUMMARY OF THE INVENTION

In accordance with the invention, apparatus for sensing and recording biopotential electrical signals associated with an anatomical body part is presented. Pick up means sense the biopotential electrical signal and coupling means couple the pick up means to circuitry means. The circuitry means includes compensation means for responding to variations in the sensed biopotential electrical signal caused by changes in either and both the pick up means and circuitry means to maintain a constant recording reference potential.

The invention further resides in battery operated power supply means which provides the necessary supply voltage for certain circuitry in the circuitry means. The battery power supply means and the certain circuitry have a first common reference potential which is isolated from and floating relative to a ground reference electrical potential to reject electromagnetic interference. Other circuitry in the circuitry means is provided the necessary supply voltage by other than the battery operated power supply means. The non-battery powered circuitry has a second common reference electrical potential which is electrically isolated from the first common reference potential.

The invention still further resides in isolator means for transmitting the sensed biopotential signals from the battery operated circuitry to the non-battery operated circuitry to provide electrical isolation between the battery and non-battery operated circuitry.

The invention further resides in means coupled to the circuitry means for displaying a signal representation of the sensed biopotential electrical signal.

BRIEF DESCRIPTION OF THE DRAWINGS

FIG. 1 is a simplified schematic diagram illustrating a polarized eyeball,

FIG. 3 shows a block diagram partly in schematic form for one sensing and recording channel of the apparatus of FIG. 2.

DETAILED DESCRIPTION

Figure 2:
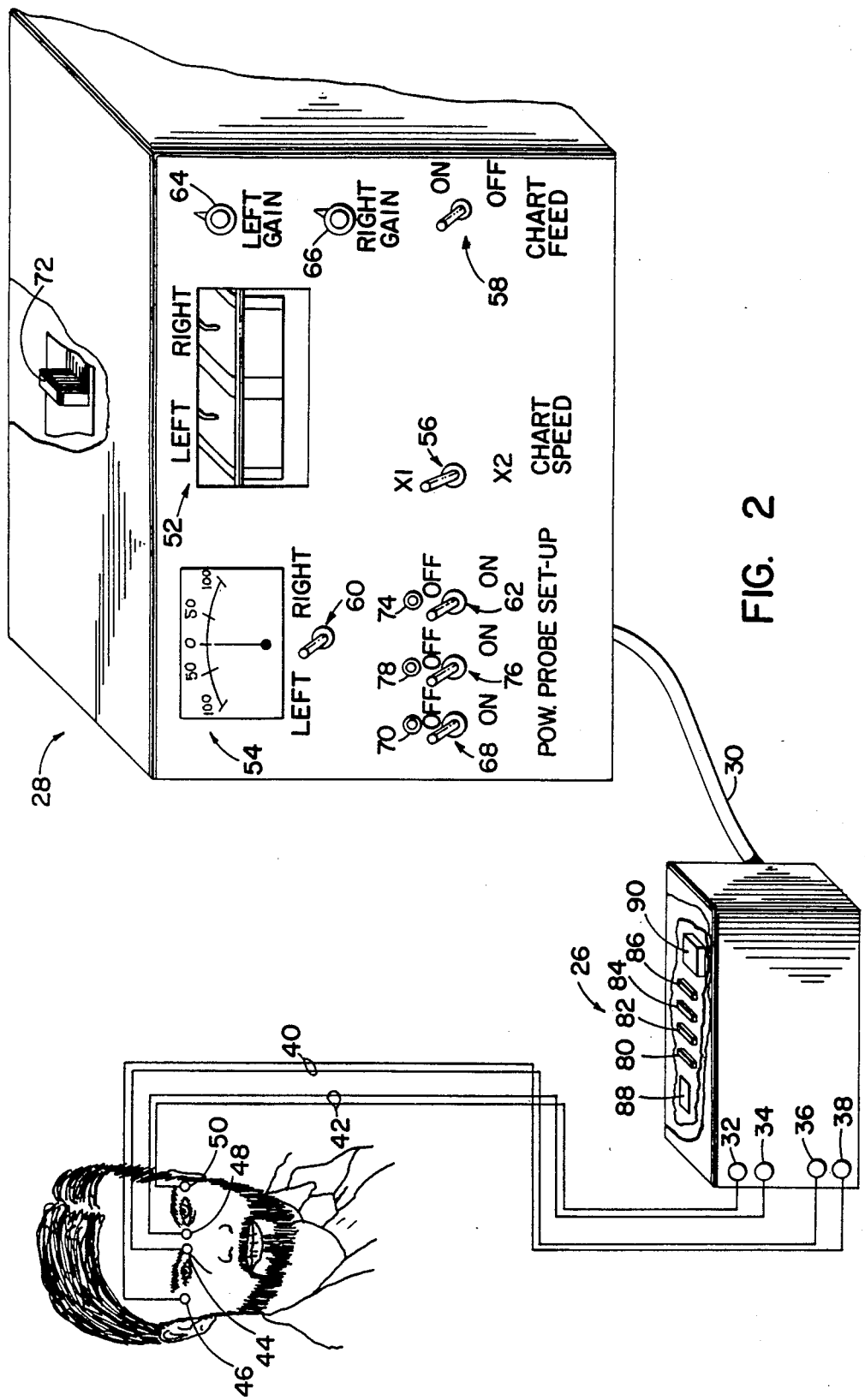
FIG. 2 shows a perspective view of apparatus embodying the present invention connected to a patient.

The present invention senses and records voltages present across the eye during eye movement. A graphic display or record of these voltages is useful in diagnosing and treating certain optometric disorders and ocular dysfunctions. However, the present invention may also be used to sense and record other anatomical biopotential electrical signals such as, for example, alpha waves generated in the skull.

FIG. 1, by way of background, is a simplified schematic diagram illustrating a polarized eyeball generally designated by the numeral 10. The eyeball 10 is electrically positive at the cornea 12 and negative at the fundus 14. Two surface electrodes 16 and 18 are placed periorbitally, one on the inner canthus and one on the outer canthus of each eye and sense the ocular standing DC potential. The electrodes 16 and 18 are connected to a galvanometer 20 or similar instrument which heretofore has been used to measure the ocular standing DC potential.

It has been reported by Sullivan in U.S. Pat. No. 3,217,706 referenced above, that an electrode placed on the cornea 12 of the eye 10 can be as much as 6 millivolts higher in DC potential than another electrode placed at its back or fundus 14. Although most of the electrical activity associated with eye movement is generated by the pigment epithelium or choroid lining the back of the retina, some also comes from the lens and cornea. The change produced in the ocular standing DC potential when the eye moves away from a precisely designated fixation reference point to another fixation target position with respect to the orbit is generally referred to as the EOG potential.

Still referring to FIG. 1, the neutral position of the eye, or the point through which a bioelectric vector passes when the eye is at rest, is referred to as the standard reference position of the eye. The standard reference position is obtained by having the patient look directly at a central fixation point (CFP) or target and is indicated generally at 22. The CFP 22 remains in a known, constant relationship with the head, when the head is in a fixed position. The potential that exists between the two periorbital electrodes 16 and 18 when the eye 10 is at this standard reference position is assumed to be the central fixation reference potential and the EOG potential is by definition zero when the eye is in this reference position. Rotation of the cornealfundic axis away from the CFP such as, for example, to another target position generally designated at 24, introduces a change in the potential across the electrodes 16 and 18. The magnitude of the potential across the electrodes 16 and 18 is approximately proportional to the angle of rotation of the eye 10.

Biopotential skin electrodes such as those made from silver-silver chloride are generally used in the art because of their desirable signal reception characteristics. The electrodes are mounted in a non-conductive shell and are recessed slightly from the surface. A suitable conductive gel is placed in the non-conductive shell such that the gel will be in contact with the electrode and the skin surface when placed upon the patient. The shell may be held in contact with the skin surface by means of double sided adhesive electrode washers. The electrodes and electrode washers are, for example, the type manufactured by IN VIVO METRIC SYSTEMS, of Healdsburg, Calif. The attachment of the electrodes and shell to the skin surface is done in accordance with the practice which is well known in the art.

Referring now to FIG. 2, a perspective view is shown of apparatus embodying the present invention as the apparatus might be connected to a patient. The apparatus includes a remote unit designated generally by the numeral 26 connected to a recording unit generally designated by the numeral 28 via a connecting cable 30. The ocular standing DC potential or electrical signal developed about the eye as the eye moves is sensed by pick up means coupled to predetermined locations about the eye. The signal is sensed by pick up means, such as, for example, electrodes 44, 46, 48, 50 and the sensed signal is coupled to and amplified by circuitry generally designated at 88 in the remote unit 26. The amplified signals are transmitted to the recording unit 28 via the cable 30.

The sensing and recording of the ocular standing DC potential has in the past often been adversely affected by and susceptible to interference from various bioelectrical signals which occur spuriously and are commonly present in clinical environments. Such signals, for example, electrocardiogram (EKG), have been superimposed upon the EOG signals. The frequency of the EOG signal generally ranges from approximately DC to 15 Hertz permitting the use of low-pass filtering in the apparatus of the present invention to reject interference from these spurious bioelectrical signals.

Because the ocular standing DC potential is of such a small magnitude, it can easily become buried in extraneous electrical noise signals and in particular, those noise signals introduced through AC operated power supplies. Even power supplies using isolation type transformers tend to introduce noise into circuitry because of the capacitive coupling between windings which provides a path between the output and the input of the transformer. Consequently, complete isolation is not obtainable. A feature of the present invention provides for certain of the circuitry 88 in the remote unit 26 to be powered by a floating reference battery power supply indicated generally by the numeral 90. The purpose and operation of the floating reference battery power supply 90 and the circuitry 88 receiving power from it will become more apparent during the discussion of FIG. 4.

In addition to being powered by the floating battery supply 90, certain of the circuitry in the remote unit 26 is connected to a floating common reference potential to electrically isolate the apparatus from the patient. One purpose of the isolation is to prevent changes in the patient's electrical potential caused by the patient coming in contact with the surroundings from influencing the magnitude of the sensed ocular standing DC potential.

Use of a floating common reference potential also minimizes the coupling of external electromagnetic noise interference into high gain DC amplification circuitry used in the remote unit 26.

Now considering the invention in more detail, the remote unit 26 has two pairs of input terminals for receiving the ocular standing DC potential sensed by the electrodes 44, 46, 48, 50. In the illustrated case, terminal pair 32,34 are associated with signals generated by the right eye and terminal pair 36,38 are associated with signals generated by the left eye. The right and left input terminal pairs are connected via leads 40 and 42 respectively to the electrodes which are adapted to be attached to the inner and outer canthi of the right eye and left eye respectively as described hereinabove. The electrodes associated with the right eye are designated 44 and 46 with electrode 44 being placed on the inner canthus and electrode 46 being placed on the outer canthus. The electrodes associated with the left eye are designated 48 and 50 with electrode 48 being placed on the inner canthus and electrode 50 being placed on the outer canthus.

A power switch 68 is operated to the ON position to connect commercial AC power to the recording unit 28. An indicator lamp 70 lights when the power switch is in the ON position. Operation of the power switch 68 also connects AC power to a double ended, transformer isolated power supply designated generally by the numeral 72. The power supply 72 provides supply voltages for various indicator lamps in the recording unit 28 as described herein and a portion of the remote unit circuitry 88.

The recording unit 28 includes means for displaying a sensed ocular standing DC potential representing signal such as, for example, a dual channel strip chart recorder generally designated by the numeral 52. A dual channel chart recorder is preferable to permit the ocular standing DC potential signal for both the right and left eyes to be recorded at the same time. The concurrent sensing and recording of both the right and left eye ocular standing DC potential permits the practitioner to more easily study and compare the eye movement recordings to determine whether or not both eyes are moving together and if they are moving correctly.

The chart recorder 52 has two chart paper feeder speeds which are selected by operating a chart speed switch 56 to one of two positions. One position, designated X1, causes the chart recorder 52 to feed chart paper at 25 millimeters per second and the second position, designated by X2, causes the chart recorder 52 to feed chart paper at 50 millmeters per second. The chart paper feeder speed is dependent upon the specific chart recorder used.

A chart feed switch 58 is used to turn the chart recorder paper feeder on and off without disconnecting the recorder portion of the chart recorder 52. This feature permits the practitioner to set up the apparatus and ready the patient for testing without running the chart paper feeder except when actually recording the ocular standing DC potential signal.

When the chart feed switch 58 is in the OFF position, relays 84 and 86 are energized by the voltage output of the isolated power supply 72 and contacts associated with the relays close to selectively connect compensation circuits in the circuitry 88. The function and operation of the relays and compensation circuits will become readily apparent during the discussion of FIG. 4.

In order to conserve energy in the batteries used in the battery power supply 90, the apparatus has a probe switch 76 mounted on the recording unit 28 which is operated to connect and disconnect the batteries to and from the battery power supply. An indicator light 78 lights when the probe switch 76 is operated to the ON position. When the probe switch 76 is in the ON position, relays 80 and 82 are energized by the voltage output of the isolated power supply 72 and contacts associated with the relays close to selectively connect the batteries to the power supply 90. When the probe switch 76 is shifted to the OFF position, relays 80 and 82 de-energize and the batteries are disconnected from the power supply 90.

Because the magnitude of electrical activity of each eye is not generally identical for the same amounts of eye movement, it is difficult to make direct comparisons of the recorded ocular standing DC potential signal for each eye. The direct comparisons are useful in diagnosing certain ocular dysfunctions. Therefore, it is desirable that the graphical representation of a sensed ocular standing DC potential exhibit equal recording pen excursions on the chart recorder graph paper for each eye when a patient fixates on a target to the right and to the left of a CFP. Equal recording pen excursions are obtained by balancing both channels of the strip chart recorder 52 to compensate for unequal recorder-amplifier gains between channels, differences in electrode sensitivities caused by differences which may exist in the electrode to skin surface contact between the right and left eye and unequal placement of the electrodes about the eyes of the patient.

Still referring to FIG. 2, the apparatus set up and channel balancing procedure is now described. An indicator lamp 74 lights when a set up switch 62 is operated to its ON position. The set up switch 62 connects a zero centered meter 54 to circuitry in the remote unit 26. Meter 54 provides the practitioner a visual indication of a patient's eye movement as the eye moves to the right or to the left of a CFP. The magnitude of the deflection of the meter 54 to the right or to the left of zero represents the percentage of chart area that will be filled during the recording of the ocular standing DC potential representative signal as the eye moves a predetermined distance to the right and left of the CFP.

After the standard reference position (neutral position of the eye) is determined, the patient fixates on a target to the right or to the left of the CFP. The right or left eye is then selected to obtain a relative measurement of the ocular standing DC potential by setting switch 60 to either the RIGHT or LEFT position. The RIGHT and LEFT positions correspond to the right and left channels respectively of the strip chart recorder 52. For an explanation purposes, it is presumed that the right eye is chosen and switch 60 is operated to the RIGHT position. The meter 54 deflects to the right of zero when the patient fixates on a target to the right of the CFP. A right gain potentiometer 66 is adjusted to cause the gain of the right channel amplifier in the strip chart recorder 52 to increase or decrease to provide the desired amount of pen excursion for the chosen fixation target position. For example, it may be desired that fixation upon a selected test target represent a 100% excursion of the recording pen on the chart recording paper. The right gain potentiometer 66 is adjusted to cause the pen excursion to fill the chart paper area at which point the meter 54 indicates 100% deflection. The switch 60 is now shifted to the LEFT position to select the left eye while the patient's eyes remain fixated on the selected test target. The meter 54 now deflects to a position representative of the pen excursion on the chart recording paper for the left eye. A left gain potentiometer 64 is adjusted to cause the meter 54 to read the same reading i.e., 100%, as obtained for the right eye. The left eye pen excursion on the chart recording paper is the same as the pen excursion for the right eye. The recording unit 28 right and left channel amplifiers are now balanced and provide equal pen excursions on the chart recording paper for each eye for eye fixation targets to the left and to the right of the CFP. The apparatus is now taken out of the set up mode by shifting switch 62 to the OFF position.

Referring now to FIG. 3, a block diagram, partially in schematic form, is shown therein for one sensing and recording channel of the apparatus shown in FIG. 2. It will be understood that a second, identical channel is required in the apparatus to permit the ocular standing DC potential for each eye to be sensed and recorded concurrently.

The ocular standing DC potential is sensed by electrodes shown generally at 100, which electrodes are adapted to be attached to a patient. The sensed signal is coupled to a low-pass filter 102 to filter out 60 Hertz interference and any additional high frequency interference electromagnetic noise signals that may be present in the sensed ocular standing DC potential. The output of the low-pass filter 102 feeds a high gain, high impedance, DC amplifier 104. The output of the amplifier 104 is coupled to a second low-pass filter 106 which provides additional low-pass filtering. The output of the filter 106 is coupled to a second DC amplifier 108. The output of amplifier 108 is coupled to a third low-pass filter 110 to provide additional filtering for the amplified ocular standing DC signal.

The output of low-pass filter 110 is fed to a buffer amplifier 116 which amplifier drives an optocoupler 118. The optocoupler 118 effectly isolates all electrical contact between its input and output. Thus the circuitry contained within the dotted line box indicated generally by the numeral 120 is electrically isolated from the patient and the remaining portions of the apparatus. Electrically isolating the amplification circuitry prevents contamination of the sensed ocular standing DC potential such as, for example, by changes in the patient reference potential caused by the patient coming in contact with his surroundings which may be at a different potential.

The output of the optocoupler 118 is fed to an impedance matching circuit 122 which matches the output impedance of the optocoupler 118 to a buffer amplifer 124. The output of buffer amplifier 124 is fed to an output DC amplifier 126. The output of amplifier 126 drives a recording pen 128 of the strip chart recorder 52 to produce on the chart recorder paper a graphical representation of the sensed ocular standing DC potential. The output of amplifier 126 is also fed to the meter 54 to provide a visual indication of relative eye movement as explained hereinabove.

To compensate for variations in the sensed ocular standing DC potential which are caused by electrode to skin surface contact changes that occur during the course of testing and apparatus set up, a first compensation means 112 is selectively connected to the output of the DC amplifier 104 through a relay contact 114. The compensation means 112 senses the output of the DC amplifier 104 during the time that relay contact 114 is closed. The compensation means 112 feeds DC amplifier 108 an input DC bias control reference voltage which control voltage is responsive to variations in the sensed ocular standing DC potential caused by electrode to skin surface contact changes.

The compensation means 112 also sets the central fixation reference potential signal transmitted to the recording pen 128 from output amplifier 126 to a midgraph reference or zero position.

When the relay contact 114 opens, the input DC bias reference to DC amplifier 108 corresponds to the changed magnitude of the sensed ocular standing DC potential signal appearing at the output of amplifier 104 and the pen recorder 128 is at mid-graph for the sensed central fixation reference potential.

A second compensation means 129 is selectively connected to the output of buffer amplifier 124 through a relay contact 130. The compensation means 129 senses the output of amplifier 124 during the time relay contact 130 is closed and produces an input DC bias control reference voltage to output amplifier 126 to compensate for drift in the output signal from the optocoupler 118 caused by temperature changes. The compensation means 129 is also responsive to changes in the sensed ocular standing DC potential caused by electrode to skin surface contact changes. When the relay contact 130 opens, the compensation means 129 produces a corrective input DC bias reference voltage to amplifier 126 to automatically compensate for pen recorder drift during the testing interval.

Figure 4:
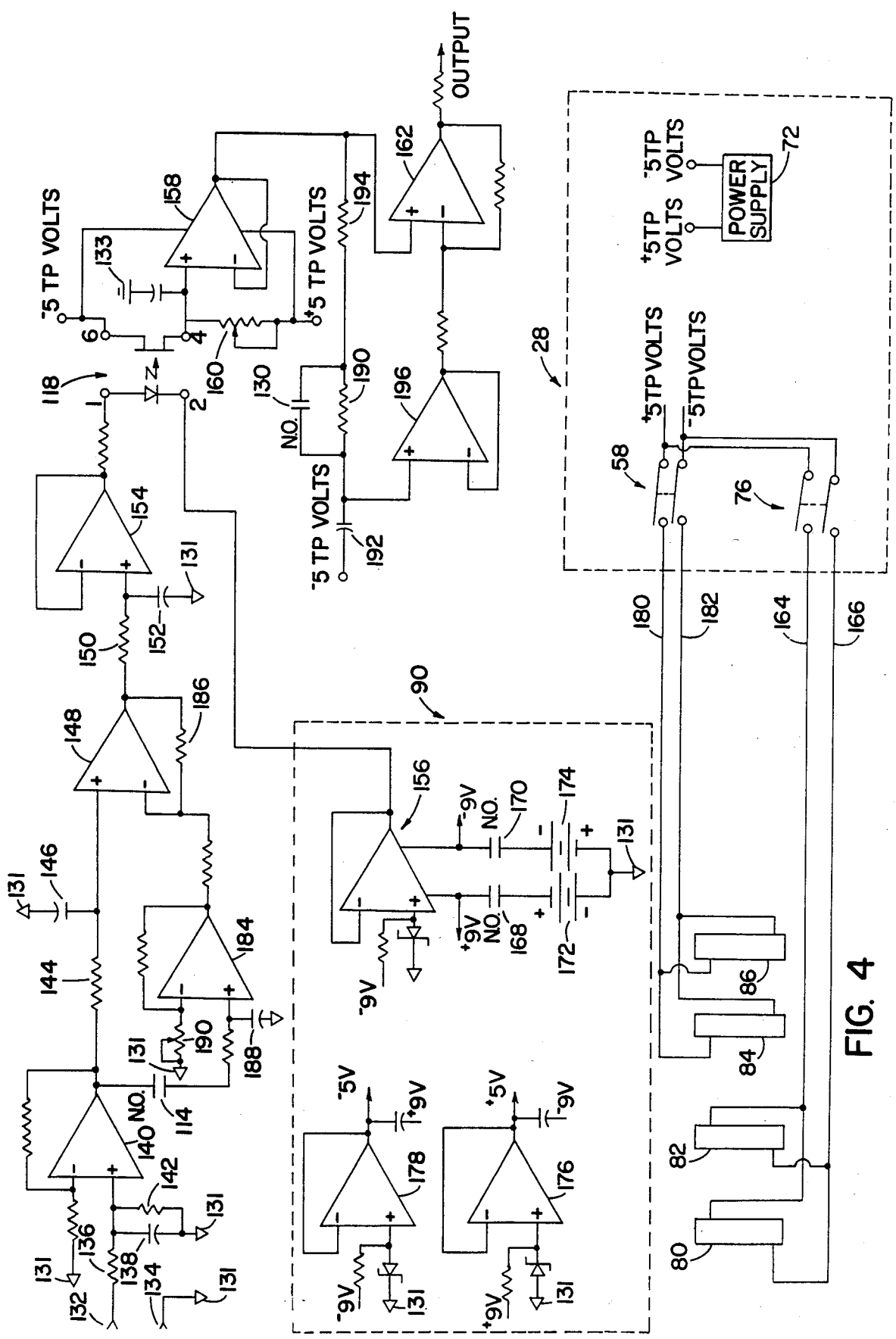
FIG. 4 shows an electrical schematic diagram of the invention in one preferred embodiment for one channel of the apparatus shown in FIGS. 2 and 3.

Referring now to FIGS. 2 and 4, a preferred electrical circuit embodying the present invention is shown in FIG. 4 in schematic form. It will be understood that the circuit diagram of FIG. 4 represents the electrical circuitry associated with one sensing and recording channel and that the circuitry is duplicated for concurrent sensing and recording of the ocular standing DC potential for each eye.

The ocular standing DC potential is sensed by electrodes as described hereinabove and the sensed ocular potential is applied across input terminals 132 and 134. Terminal 134 is connected to a floating common reference potential generally designated at 131. The sensed ocular standing DC potential signal is coupled to and passes through a low-pass filter comprised of resistor 136 and capacitor 138. The values of resistor 136 and capacitor 138 are chosen such that the cutoff frequency of the low-pass filter is approximately 10 Hertz.

The sensed ocular signal is fed from the resistor 136 to the non-inverting terminal of a high gain, high impedance DC amplifier 140 which amplifier has a voltage gain of 100. Because the input to DC amplifier 140 has such a high impedance, a very high value resistance 142 is connected between the non-inverting terminal of amplifier 140 and the floating common reference potential 131 to provide a minimum load to the input of amplifier 140. The DC amplifier 140 is designed to have a six microvolt sensitivity at its input.

The output signal from amplifier 140 is passed through a second low-pass filter comprised of resistor 144 and capacitor 146. The values of resistor 144 and capacitor 146 are chosen to provide a cut-off frequency of approximately 15 Hertz. The output of the low-pass filter comprised of resistor 144 and capacitor 146 is coupled to the non-inverting input of a second DC amplifier 148.

The output of amplifier 148 is fed to a third low-pass filter comprised of resistor 150 and capacitor 152. The values of resistor 150 and capacitor 152 are chosen to provide a cut-off frequency not to exceed 20 Hertz. The output of the low-pass filter comprised of resistor 150 and capacitor 152 is fed to the non-inverting input of a buffer amplifier 154.

The voltage signal representation of the ocular standing DC potential appearing at the output of the buffer amplifier 154 is a bipolar voltage signal having in the present circuit design a maximum magnitude equal to 5 volts; that is, the voltage signal at the output of amplifier 154 swings a maximum of 5 volts above and below the floating common reference potential 131.

Because the DC amplifiers 140, 148 and 154 are referenced to the floating common reference potential 131, there is no DC bias in the voltage signal at the output of amplifier 154. The presence of a DC bias voltage in the output signal of amplifier 154 produces an offset in the mid-graph reference level which appears as unequal pen excursions for equal eye movements. Thus, if an offset is present in the recording the practitioner could incorrectly diagnose an ocular dysfunction when, in actuality, none exists.

The amplifier 154 output signal is fed to the input of an optocoupler 118. The optocoupler 118 consists of an infrared emitting diode (LED) connected between input terminals 1 and 2 coupled to a symetrical bilateral silicon photo detector connected between terminals 4 and 6. The photo detector is electrically isolated from the input and performs like an ideal isolated FET. The optocoupler 118 is of the type, for example, manufactured by the General Electric Company Model H11F1, and is designed for distortion free control of low level DC analog signals.

Terminal 2 of the optocoupler 118 is connected to a negative voltage with respect to the most negative voltage that is expected to appear at terminal 1 such that the LED has an approximate 1 volt biasing potential. The bias voltage at terminal 2 is approximately minus 6 volts DC for the present circuit and is produced by a low power regulator 156. Regulator 156 is designed in a conventional manner well known in the art.

The output signal of the optocoupler 118 appearing across terminals 4 and 6 is fed to a buffer amplifier 158. The buffer amplifier 158 has a variable resistance 160 connected between its non-inverting terminal and +5 volts. Terminal 6 of the optocoupler 118 is connected to −5 volts. The ±5 volts are produced by the isolated power supply 72 in the recording unit 28 and provide the necessary supply voltages for amplifier 158. The variable resistance 160 is used to match the output impedance of the optocoupler 118 to the input impedance of the buffer amplifier 158.

The output of buffer amplifier 158 is fed to a DC voltage amplifier 162. The output of the amplifier 162 drives a recording pen in the strip chart recorder 52 with a voltage that is representative of the sensed ocular standing DC potential.

Because the output of the optocoupler 118 is electrically isolated from its input and the sensed ocular standing DC potential signal is now amplified to a sufficient magnitude to be relatively immune to electromagnetic noise influences, a conventional electrical ground potential generally designated at 133 is used as the signal reference level for the circuitry driving the recording pen.

Operation of the probe switch 76 as described hereinabove connects leads 164 and 166 across the ±5 volt outputs of the isolated power supply 72. Operating the probe switch to the ON position causes relays 80 and 82 to energize and provide a contact closure to relay contact 168 and 170 respectively. The contact closures connect 9 volt batteries 172 and 174 to the voltage regulator 156 and to voltage regulators 176 and 178. Voltage regulators 176 and 178 produce ±5 volts respectively. As can be seen in FIG. 4, the batteries are referenced to the floating common reference potential 131. The batteries 172 and 174, and the voltage regulators 156, 176 and 178 comprise the floating reference battery power supply 90. Consequently, the voltages supplied by the supply 90 also move relative to variations in the sensed ocular standing DC potential caused by electrode to skin contact changes and electromagnetic noise interference to help compensate for the change and reject interference.

As indicated hereinabove, operation of the chart feed switch 58 to the OFF position energizes relays 84 and 86 by connecting ±5 volts of power supply 72 to leads 180 and 182 respectively. The operation of the chart feed switch 58 to the OFF position activates the compensation circuits which are described as follows.

Still referring to FIGS. 2 and 4, a high input impedance DC amplifier 184 is connected to the output of the high gain, high impedance amplifier 140 through the closed relay contact 114. The output of amplifier 184 is connected to the inverting terminal of DC amplifier 148. The output of amplifier 148 is fed back through the feedback resistor 186 to the inverting terminal of the amplifier 148 and the inverting terminal of amplifier 184.

The output signal from DC amplifier 140 charges a specially designed low-leakage capacitor 188 to the voltage magnitude appearing at the output of the DC amplifier 140. A variable resistance 190 is connected between the inverting terminal of amplifier 184 and the common reference potential 131. Resistance 190 is adjusted so that the output signal from amplifier 184 provides a DC bias reference voltage to the inverting input terminal of DC amplifer 148 to cause the central fixation reference potential recorded on the chart recorder chart paper to be zero when the patient fixates upon a CFP.

The voltage charge on capacitor 188 continuously follows the voltage output of amplifier 140 and automatically provides a changing DC bias reference voltage to the inverting terminal of amplifier 148 to maintain the zero reference level established. This feature frees the practitioner from constantly rezeroing the apparatus to compensate for drift caused by electrode to skin surface contact changes occurring during the set up interval.

Also, during the time that the chart feed switch 58 is in the OFF position, relay 86 is energized causing relay contact 130 to close. Relay contact 130 is in parallel with resistor 190. The output of buffer amplifier 158 is connected through resistor 194 in series with resistor 190 to the non-inverting terminal of buffer amplifier 196. A capacitor 192 is connected between the non-inverting terminal of buffer amplifier 196 and −5 volts of power supply 72. The capacitor 192 charges to the output voltage of buffer amplifier 158 and provides the DC bias level to amplifier 196.

The output of buffer amplifier 196 is fed to the inverting terminal of the DC amplifier 162 to provide the DC bias to the input of the amplifier 162. Consequently, the capacitor 192 charges to the amplifier 158 output voltage through resistor 194 and the closed relay contact 130 to the voltage level present at the amplifier 158 output. The voltage charge on the capacitor 192 establishes an input DC bias level for amplifier 162 by way of buffer amplifier 196 which bias level corresponds to the zero reference level set during the central fixation reference level zeroing procedure described above.

When the chart feed switch 58 is shifted to the ON position relays 84 and 86 de-energize causing relay contacts 114 and 130 respectively to open. The voltage charge stored in capacitor 188 is representative of the ocular standing DC potential signal from DC amplifier 140. The voltage charge on capacitor 192 provides a very slight zero correction to compensate for very slow drift in the ocular standing DC potential caused by changes in the electrode to skin surface contact during the testing interval. This slight zero correction compensation keeps the chart recording pen from drifting off the chart recording paper during testing. This feature permits a longer testing interval before rezeroing is required.

Apparatus for sensing and recording biopotential electrical signals about the eyes has been described in one preferred embodiment; however, biopotential electrical signals associated with other anatomical parts may also be sensed and recorded by the apparatus of the present invention. Consequently, numerous modifications and changes may be had without departing from the spirit of the invention. Therefore, the invention has been described by way of illustration rather than limitation.

I claim:

1. Apparatus for sensing and recording an ocular standing DC potential, said apparatus comprising:
   electrode means, adapted to be connected to the inner and outer canthi of a patient's eye, for sensing the voltage difference across the patient's eye wherein said sensed voltage difference is indicative of eye movement across the eye socket;
   a first low pass filter means for filtering the voltage difference sensed by output of said electrode means;
   first DC amplification means for amplifying the output of said first low pass filter means;
   a second low pass filter means for filtering the output of said first DC amplification means;
   second DC amplification means for amplifying the output of said second low pass filter means;
   first selective compensation means connected between the output of said first DC amplification means and the output of said second DC amplification means for producing a first control reference voltage responsive to variations in said sensed ocular standing DC potential caused by electrode means to skin surface contact changes, said second DC amplification means being responsive to said first control reference voltage for maintaining a zero central fixation reference potential;
   a third low-pass filter means for filtering the output of said second DC amplification means;
   isolator means coupled to the output of said third low pass filter means for transmitting the output of said third low-pass filter means;
   third DC amplification means coupled to the output of said isolator means for amplifying the same;
   fourth DC amplification means for amplifying the output of said third DC amplification means to provide an output signal representative of said sensed ocular standing DC potential,
   second selective compensation means connected between the output of said third DC amplification means and the output of said fourth DC amplification means for producing a second control reference voltage responsive to variations in said sensed ocular standing DC potential caused by at least one of said electrode means to skin surface contact changes and drift in said isolator means output caused by temperature changes, said fourth DC amplification means being responsive to said second control reference voltage for maintaining a zero fixation reference potential, and means for recording the output signal representative of the ocular standing DC potential.

2. Apparatus for sensing and recording an ocular standing DC potential as defined in claim 1 further comprising:
   battery operated power supply means for supplying the necessary supply voltage for certain circuitry in a remote unit wherein said battery operated remote unit circuitry includes said first and said second DC amplification means, said first selective compensation means and said isolator means input; said battery operated power supply means and said battery operated remote unit circuitry having a first common reference electrical potential, and transformer isolated power supply means for supplying the necessary supply voltage for the remaining circuitry in said remote unit and the circuitry of a recording unit, and said remaining circuitry of said remote unit and said circuitry of said recording unit being AC operated circuitry, wherein said AC operated circuitry includes said third and said fourth DC amplification means, said second selective compensation means and said isolator means output; said transformer isolated power supply means and said AC operated circuitry having a second common reference electrical potential wherein said second common reference potential is electrically isolated from said first common reference potential.

3. Apparatus for sensing and recording an ocular standing DC potential as defined in claim 2 wherein said first common reference electrical potential is isolated from a ground reference electrical potential and is floating relative to said second common reference potential.

4. Apparatus for sensing and recording an ocular standing DC potential as defined in claim 3 wherein said second common reference potential is a ground reference electrical potential.

5. Apparatus for sensing and recording an ocular standing DC potential as defined in claim 1 further comprising: said means for displaying a signal representative of said sensed ocular standing DC potential.

6. Apparatus for sensing and recording an ocular standing DC potential as defined in claim 5 wherein said means for recording includes a strip chart recorder.

7. Apparatus for sensing electrical signals across the eye during eye movement, said apparatus comprising:
pick up means for sensing the electrical signals about an eye;
DC circuitry;
coupling means for coupling said pick up means to said circuitry;
said DC circuitry comprising means for processing said sensed electrical signals and including compensation means for responding to variations in said sensed electrical signals caused by changes in at least one of said pick up means and said circuitry to maintain a zero central fixation reference potential;
said compensation means including battery operated power supply means for providing the necessary supply voltage for certain circuitry in said DC circuitry, said battery power supply means and said certain circuitry having a first common reference electrical potential, said first common reference potential having a floating electrical potential relative to a ground reference electrical potential to reject electromagnetic interference, and
said DC circuitry further including circuitry other than said certain circuitry, said other circuitry being provided the necessary supply voltage by means other than said battery operated power supply means, said non-battery operated circuitry having a second common reference electrical potential, said second common reference potential being electrically isolated from said first common reference potential.

8. Apparatus for sensing electrical signals as defined in claim 7 wherein said circuitry includes isolator means for transmitting said sensed electrical signals from said battery operated circuitry to said non-battery operated circuitry to provide electrical isolation between said battery operated and non-battery operated circuitry.

9. Apparatus for sensing electrical signals as defined in claim 7 further comprising:
means coupled to said circuitry for displaying a signal representation of said sensed electrical signals.

10. Apparatus for sensing electrical signals as defined in claim 7 further comprising:
means for recording said sensed electrical signals.

11. Apparatus for sensing biopotential electrical signals, said apparatus comprising:
pick up means for sensing a biopotential electrical signal generated by an anatomical body part;
first circuitry;
second circuitry; coupling means for coupling said pick up means to said first circuitry comprising means for processing said sensed biopotential electrical signals and;
said first and second circuitry including compensation means for responding to variations in said sensed biopotential electrical signal caused by changes in at least one of said pick up means and said first and second circuitry to maintain a constant recording reference potential;
said compensation means further including battery operated power supply means for providing the necessary supply voltage for certain circuitry in said first circuitry, said battery power supply means and said certain circuitry having first common reference electrical potential, said first common reference potential having a floating electrical potential relative to a ground reference electrical potential to reject electromagnetic interference;
said second circuitry being provided the necessary supply voltage by means other than said battery operated power supply means, said non-battery operated circuitry having a second common reference electrical potential, said second common reference potential being electrically isolated from said first common reference potential, and
isolator means for transmitting said sensed biopotential electrical signal from said first circuitry to said second circuitry to provide electrical isolation between said first and second circuitry.

12. Apparatus for sensing a biopotential electrical signal as defined in claim 11 further comprising:
means coupled to said circuitry for displaying a signal representation of said sensed biopotential electrical signal.

13. Apparatus for sensing a biopotential electrical signal as defined in claim 11 wherein said anatomical body part is an eye.

14. Apparatus for sensing a biopotential electrical signal as defined in claim 13 wherein said pick up means is a biopotential electrode.

* * * * *